(12) United States Patent
Nakagawa et al.

(10) Patent No.: US 8,277,752 B2
(45) Date of Patent: Oct. 2, 2012

(54) OPTICAL MEASUREMENT APPARATUS

(75) Inventors: Takashi Nakagawa, Kyoto (JP); Shinya Nakajima, Kyoto (JP); Tokuo Kasai, Kyoto (JP); Kazuhiro Ohmiya, Kyoto (JP)

(73) Assignee: ARKRAY, Inc., Kyoto-shi (JP)

( * ) Notice: Subject to any disclaimer, the term of this patent is extended or adjusted under 35 U.S.C. 154(b) by 145 days.

(21) Appl. No.: 12/517,765

(22) PCT Filed: Nov. 20, 2008

(86) PCT No.: PCT/JP2008/071140
§ 371 (c)(1),
(2), (4) Date: Jun. 4, 2009

(87) PCT Pub. No.: WO2010/058473
PCT Pub. Date: May 27, 2010

(65) Prior Publication Data
US 2011/0058993 A1    Mar. 10, 2011

(51) Int. Cl.
*G01N 31/22* (2006.01)
*G01N 21/75* (2006.01)
*G01N 21/00* (2006.01)
*C12M 1/36* (2006.01)

(52) U.S. Cl. .............. 422/403; 422/63; 422/64; 422/65; 422/66; 422/67; 422/400; 422/401; 422/402; 422/404; 422/408; 422/420; 422/421; 422/425; 422/430; 435/286.1; 435/286.2; 435/287.1; 435/287.2; 435/287.9; 436/164; 436/169; 436/170

(58) Field of Classification Search ........................ None
See application file for complete search history.

(56) References Cited

U.S. PATENT DOCUMENTS

| | | | |
|---|---|---|---|
| 5,077,010 A * | 12/1991 | Ishizaka et al. ............... | 422/408 |
| 5,316,727 A | 5/1994 | Suzuki et al. | |
| 5,885,839 A | 3/1999 | Lingane et al. | |
| 7,141,212 B2 | 11/2006 | Catt et al. | |
| 2006/0246596 A1 | 11/2006 | Jaunakais | |
| 2008/0019871 A1 | 1/2008 | Sakamoto et al. | |

FOREIGN PATENT DOCUMENTS

| | | |
|---|---|---|
| CN | 1304490 A | 7/2001 |
| EP | 0922954 A2 | 6/1999 |
| EP | 1096256 A1 | 5/2001 |
| JP | 59-10850 | 1/1984 |
| JP | 3-95433 | 4/1991 |
| JP | 5-5736 | 1/1993 |
| JP | 8-110342 | 4/1996 |
| JP | 9-127120 | 5/1997 |
| JP | 10-274624 | 10/1998 |
| JP | 2001-318101 | 11/2001 |
| JP | 2004-317211 | 11/2004 |
| JP | 2006-250787 | 9/2006 |
| WO | 99/35487 A1 | 7/1999 |
| WO | WO 2006/059694 | 6/2006 |

* cited by examiner

Primary Examiner — Neil N Turk
(74) Attorney, Agent, or Firm — Fox Rothschild LLP

(57) ABSTRACT

An optical measurement apparatus is provided for conducting a test by efficiently reading color development of a reagent after reaction by optical measurement.

To the above end, an optical measurement apparatus is provided which is to be used with at least one test instrument mounted to the apparatus. The test instrument includes a carrier provided with at least one reagent retaining portion which retains a reagent, and a sample is applied to the carrier. The optical measurement apparatus includes a reader for reading color development of the reagent retaining portion, and a controller for performing driving control of the reader and determination. The controller performs the determination by utilizing data obtained by a reading operation P to read the color development of the reagent performed after the lapse of a reaction completion period Tr1-Tr6 from the mounting of the test instrument, and the reaction completion period depends on the reagent.

11 Claims, 10 Drawing Sheets

京都太郎　CH1　FluA: (+)1
　　　　　　　　FluB: —

2007/10/31 09:02-09:17
ID:1234567890123457

京都花子　CH2　FluA: +
　　　　　　　　FluB: **

2007/10/31 09:04-09:19
ID:1234567890123458

関西太郎　CH3　FluA: (+)1
　　　　　　　　FluB: —

2007/10/31 09:06-09:21
ID:1234567890123459

関西花子　CH4　FluA: +
　　　　　　　　FluB: **

2007/10/31 09:08-09:23
ID:1234567890123460

大和太郎　CH5　FluA: —
　　　　　　　　FluB: —

2007/10/31 09:10-09:25
ID:1234567890123491

大和花子　CH6　FluA: +
　　　　　　　　FluB: **

OPTICAL MEASUREMENT APPARATUS

TECHNICAL FIELD

The present invention relates to an optical measurement apparatus for conducting a test by optically reading the color development of a reagent.

BACKGROUND ART

Nowadays, various measurement apparatuses are used for POCT (Point of Care Testing) to be performed at hospitals, clinics, homes, etc., without relying on clinical examination specialists. Examples of such apparatuses include clinical examination apparatuses (see e.g. Patent Document 2) for performing optical reading with respect to an urine test strip (see e.g. Patent Document 1) once dipped in urine, or with respect to a biochemical test piece to which blood serum or blood plasma has been applied. Other examples are optical measurement apparatuses for performing measurement with respect to a cuvette (see e.g. Patent Document 3) with a liquid reagent contained.

FIG. 10 shows an example of conventional optical measurement apparatus (see e.g. Patent Document 4). To the illustrated optical measurement apparatus X, a test instrument Y for immunochromatography is mounted. The test instrument Y is a test piece in the form of a strip provided with a porous carrier 91. The porous carrier includes a plurality of reagent retaining portions 92 which retain a reagent (an immunologic substance, mainly an antibody) fixed to the portion. When a liquid sample such as blood or urine to be analyzed is applied to part of the test instrument Y, the sample infiltrates into the porous carrier 91. When the sample moving through the carrier reaches the reagent retaining portions 92, the sample reacts with the reagent. As a result, the reagent retaining portions 92 develop a color in accordance with the concentration of a particular component contained in the sample.

FIG. 11 shows a typical urine test strip to be used by dipping in urine. The illustrated test strip 910 includes a base 911 in the form of a strip, and reagent retaining portions 912. Each reagent retaining portion 912 is provided on the base 911 and includes a carrier made of a porous matrix such as filter paper in which a reagent is fixed in an impregnated and dried state. When the reagent retaining portion 912 of the test strip 910 is dipped in a urine sample collected in e.g. a paper cup and pulled out, the urine sample infiltrated in the reagent retaining portion 912 through the carrier reacts with the reagent. After the lapse of a predetermined reaction period, the color development of the reagent retaining portion 912 is checked.

FIG. 12 shows an example of conventional optical measurement apparatus for the measurement of a biochemical test piece including a reagent retaining portion to which a sample of urine or blood serum/blood plasma extracted from blood is to be directly applied. The illustrated optical measurement apparatus 920 includes a table 922 on which biochemical test pieces 921 are to be mounted. Each test piece 921 includes a carrier made of at least one of a high polymer compound (e.g. paste represented by water-soluble polymer) and a porous film (such as knit fabric or nonwoven fabric). The reagent retaining portion is provided by fixing a reagent to at least one of the high polymer compound and the porous film in a dry state. To perform measurement using the optical measurement apparatus 920, a liquid sample such as blood or urine to be analyzed is directly applied to the reagent retaining portion of the test piece 921. The sample dissolves the high polymer compound forming the carrier or infiltrates into the porous film. Thus, the sample reacts with the reagent in the reagent retaining portion. After the lapse of a predetermined reaction period, the color development of the reagent retaining portion is checked.

FIG. 13 shows an example of test instrument of a cuvette type. The test instrument 930 shown in the figure includes a plurality of wells 931 and is made of e.g. a light-transmitting resin. Each of the wells 931 is used as a carrier, and a reagent retaining portion is provided by sealing a reagent in a liquid or solid state in the well 931. When a sample is put into a selected one of the wells 931 of the test instrument 930, the sample reacts with the reagent in the well 931. After a predetermined period of time, the well 931, which functions as the reagent retaining portion, develops a color in accordance with the concentration of a particular component contained in the sample. Since the well 931 transmits light, the color development is easily checked from the outside.

Referring again to FIG. 10, the optical measurement apparatus X includes a light emitting means 93 and a light receiving means 94. When the test instrument Y is mounted to the optical measurement apparatus X, an instruction to start the test is given to the controller 95 by e.g. the user's operation. The controller 95 performs the light emitting operation for lighting the light emitting means 93 and the light receiving operation for receiving the light reflected by the porous carrier 91 including the reagent retaining portion 92 at the light receiving means 94. By the signal transmission from the light receiving means 94 to the controller 95, the image data of the reagent retaining portions 92 of the porous carrier 91 are stored in the controller 95. By analyzing the image data which corresponds to the color development of the reagent retaining portions 92, the presence or absence of a particular component in the sample is determined.

Though not illustrated, when the test instrument Y is an urine test strip similar to the test strip 910 shown in FIG. 11 or a biochemical test piece, the light reflection during or after the reaction of the sample with the reagent on the surface of the reagent retaining portion 912 (sometimes called a reagent pad) is measured by an exclusive device. When the test instrument Y is of a cuvette-type similar to the test instrument 930 shown in FIG. 13, the light reflection or light transmission after the reaction of the sample with the reagent in the well is measured through the light-transmitting surface of the well.

The test results obtained by the optical measurement are outputted by an output means 96 such as a printer. Based on the output results, the user can recognize the presence or absence of a particular component in the sample.

After a sample is applied to the test instrument Y, it takes some time before the reaction progresses to such a degree that proper testing is possible, and this reaction completion time varies depending on the kind or amount of the reagent. Thus, after the sample is applied to the test instrument Y, the user needs to measure the time until the testing by e.g. the optical measurement apparatus X becomes possible. To avoid this, the optical measurement apparatus shown in FIG. 12 is designed to automatically perform the pipetting, i.e., application of the sample to the test piece 921, the measurement of the reaction completion time and the measurement of the color development after the lapse of the reaction completion time. Thus, the user just needs to put an unused test piece 921 and a container containing a sample into the optical measurement apparatus 920.

However, in e.g. a simple measurement apparatus without a pipetting function or a small measurement apparatus in which a sample obtained from a patient is not to be stored, the sample is not automatically applied to the test instrument Y.

To use such a measurement apparatus, as described above, the user needs to apply the sample to the test instrument Y manually (by dipping in the case of a urine test strip or dropping using a pipette in the case of a test piece or a cuvette) and then mount the test instrument Y to the measurement apparatus. To manually apply the sample to the test instrument Y and further measure the time is a burden on the user.

For instance, tests for influenza by immunochromatography may need to be performed with respect to a large number of patients in one hospital for a short period of time. In such a case, samples obtained from the large number of patients may be applied to test instruments Y at different timings, and the reaction completion time needs to be measured with respect to each of the test instruments. Further, to smoothly perform the testing of the test instruments Y, the timing of application of the sample to each test instrument Y needs to be varied intentionally.

In tests for allergy by immunochromatography, each patient may be tested for a plurality of allergy items. In such a case, a sample obtained from one patient is applied to a plurality of test instruments Y. Since the test items to be tested by the test instruments Y differ from each other, the reaction completion time for proper testing may differ among the test instruments. Thus, while successively mounting test instruments to the optical measurement apparatus X, the user needs to measure the reaction completion time which differ among the test instruments, and such work is a burden on the user. Such problems related to the reaction time and the time of application of the sample occur also in the testing of a urine test strip, a biochemical test piece and a cuvette type test instrument.

Patent Document 1: PCT WO2006/059694
Patent Document 2: JP-A-09-127120
Patent Document 3: JP-A-2001-318101
Patent Document 4: JP-A-2006-250787

DISCLOSURE OF THE INVENTION

Problems to be Solved by the Invention

The present invention has been proposed under the circumstances described above. It is, therefore, an object of the present invention to provide an optical measurement apparatus for conducting a test by efficiently reading color development of a reagent after reaction by optical measurement.

Means for Solving the Problems

According to the present invention, there is provided an optical measurement apparatus to be used with at least one test instrument mounted to the apparatus, where the test instrument includes a carrier to which a sample is applied, and the carrier is provided with at least one reagent retaining portion for retaining a reagent. The optical measurement apparatus comprises a reader for reading color development at the reagent retaining portion, and a controller for performing driving control of the reader and for making a determination. The controller performs the determination by utilizing data obtained by reading the color development of the reagent after the mounting of the test instrument and lapse of a reaction completion period depending on the reagent. The "reaction completion period" in this embodiment may be a period of time taken until the color change of the reagent due to the reaction with the sample has been completed and stopped, or a period of time taken until the color development progresses to such a degree that shows sufficient reaction of the reagent with the sample. In the latter case, the color of the reagent may still change even after the lapse of the reaction completion time.

In a preferred embodiment of the present invention, the reaction completion period may be set by reading test item information recorded on the test instrument and utilizing the test item information.

In a preferred embodiment of the present invention, the apparatus may further comprise a sensor for detecting the mounting of the test instrument.

In a preferred embodiment of the present invention, the apparatus may be so designed that a plurality of test instruments are mounted.

In a preferred embodiment of the present invention, the apparatus may be so designed that the plurality of test instruments are mounted in a row, and the reader scans the plurality of test instruments in the direction in which the row extends.

In a preferred embodiment of the present invention, the reader may perform scanning after the mounting of the test instruments and before the lapse of the reaction completion period.

In a preferred embodiment of the present invention, the reader may perform reading of the color development of the reagent retaining portion at least once after the mounting of the test instrument and before the lapse of the reaction completion period. When reaction of the sample with the reagent is determined to be completed as a result of preliminary determination based on the data obtained by the reading, the controller adopts the preliminary determination result as the determination result of the test instrument.

In a preferred embodiment of the present invention, the test instrument may be a test piece for immunochromatography, and the carrier may comprise a porous film. The reagent retaining portion may be provided by fixing an immunologic substance to the porous film.

In a preferred embodiment of the present invention, the test instrument may be a test strip to be dipped in a liquid. The carrier may comprise a porous film, and the reagent retaining portion may be provided by fixing an immunologic substance in a dry state to the porous film.

In a preferred embodiment of the present invention, the test instrument may be a test piece which is so designed that a sample is to be dropped onto the reagent retaining portion. The carrier may comprise at least one of a high polymer compound and a porous film, and the reagent retaining portion may be provided by fixing the reagent in a dry state to at least one of the high polymer compound and the porous film.

In a preferred embodiment of the present invention, the test instrument may be a light-transmitting cuvette including a plurality of compartments, and the carrier may comprise a light-transmitting compartment. The reagent retaining portion may be provided by sealing the reagent in a liquid or solid state in the compartment.

Other features and advantages of the present invention will become more apparent from the detailed description given below with reference to the accompanying drawings.

BRIEF DESCRIPTION OF THE DRAWINGS

FIG. 6 is a plan view of the sheet showing the results of the test performed with the optical measurement apparatus shown in FIG. 1.

BEST MODE FOR CARRYING OUT THE INVENTION

Preferred embodiments of the present invention will be described below with reference to the accompanying drawings.

Figure 1:
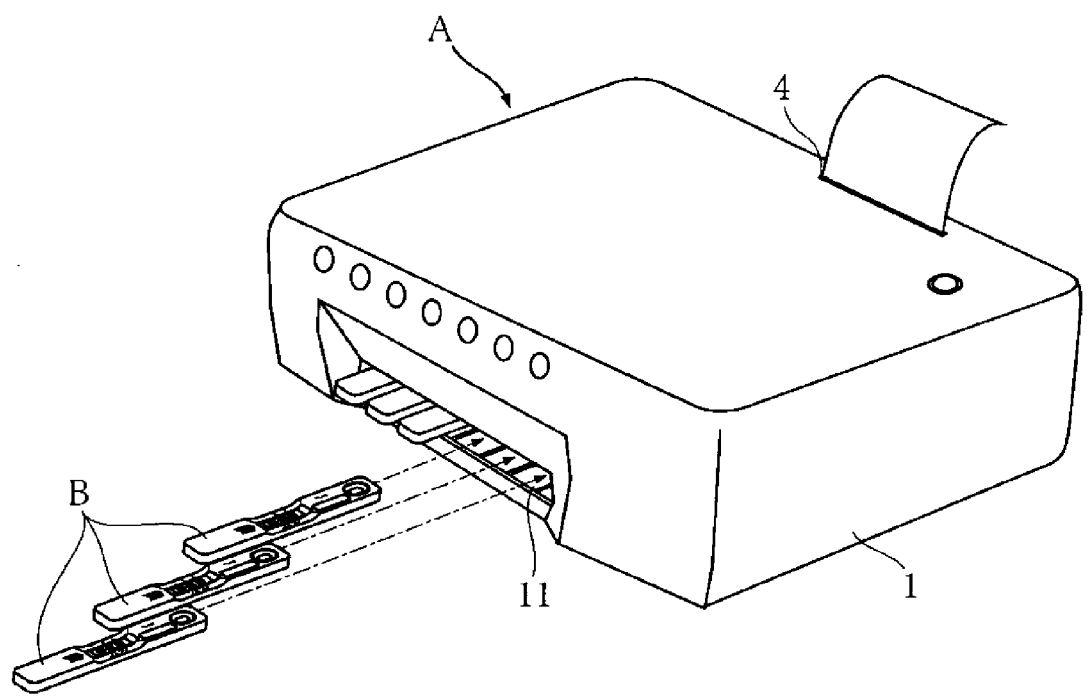
FIG. 1 is an overall perspective view showing an example of optical measurement apparatus according to the present invention.
Figure 2:
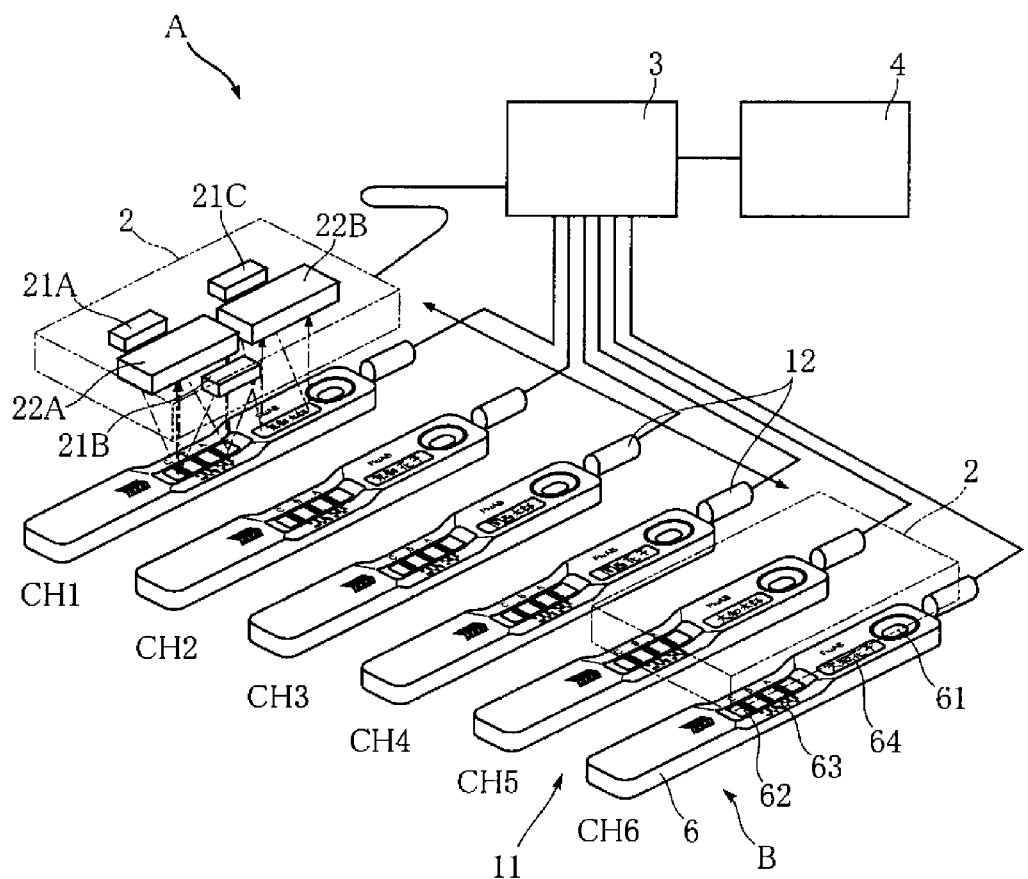
FIG. 2 is a system structure diagram of the optical measurement apparatus shown in FIG. 1.

FIGS. 1 and 2 show an example of optical measurement apparatus according to the present invention. The optical measurement apparatus A of this embodiment includes a case 1, a reader 2, a controller 3 and a printer 4. The apparatus is designed to conduct a test by immunochromatography by reading a test instrument B mounted to the apparatus. In FIG. 2, the illustration of the case 1 is omitted for easier understanding.

Figure 3:
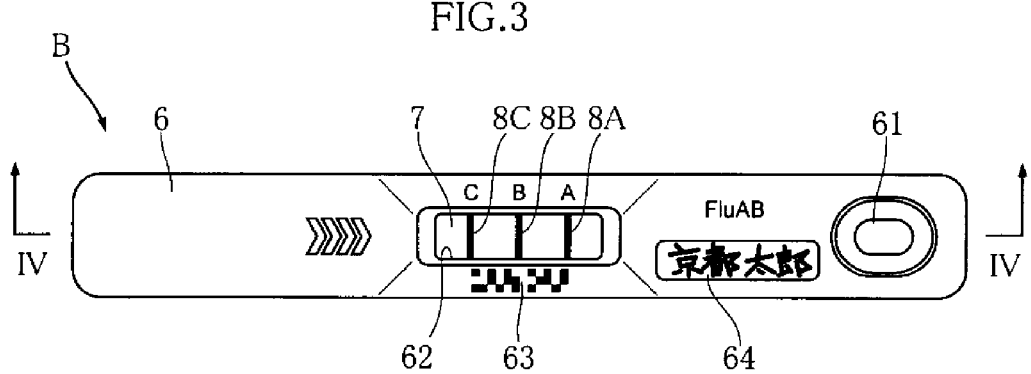
FIG. 3 is a plan view showing an example of test piece to be mounted to the optical measurement apparatus of FIG. 1.
Figure 4:
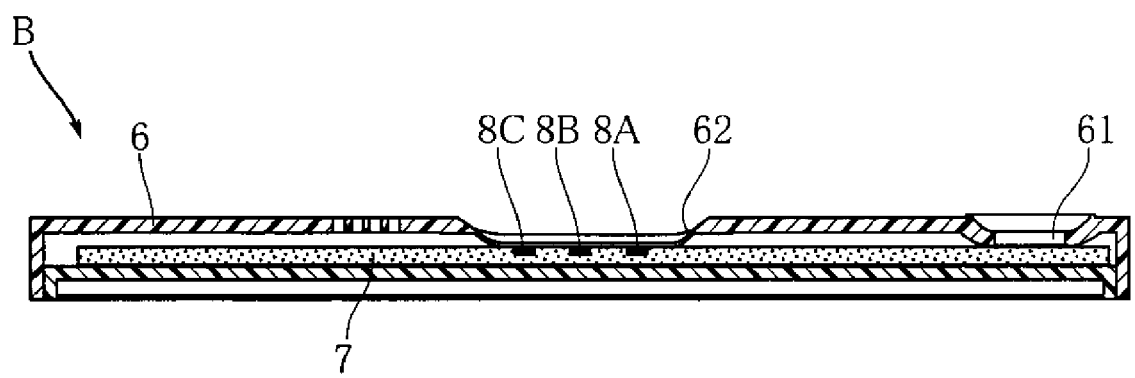
FIG. 4 is a sectional view taken along lines IV-IV in FIG. 3.

FIGS. 3 and 4 show a test instrument B to be mounted to the optical measurement apparatus A. In the test instrument B, a sample applied to the instrument reacts with a reagent. The test instrument has a shape and size suitable for the testing using the optical measurement apparatus A. The test instrument B includes a case 6, a carrier 7 and reagent retaining portions 8A, 8B, 8C to which an immunologic substance such as an antibody is fixed. The test instrument B illustrated in the figure is of a type to be used for e.g. tests for influenza.

The case 6 has an elongated shape made of e.g. a white resin and accommodates the carrier 7 made of a porous matrix. The case 6 includes an application portion 61, a measurement window 62, a test item code 63 and a patient information entry section 64. The application portion 61 is a portion to which a sample is to be applied. The application portion comprises a through-hole exposing an end of the carrier 7 and a crater-shaped portion surrounding the through-hole. The measurement window 62 comprises an elongated through-hole formed at the center of the case 6 and exposes the reagent retaining portions 8A, 8B, 8C formed at the carrier 7. The test item code 63 is provided for indicating the test item which can be tested by the test instrument B and may be a printed barcode (two-dimensional code in the figure). The patient information entry section 64 is a region in which information such as the name of the patient who is taking the test is to be written by hand.

Though not illustrated, when the test instrument B is a urine test strip, the case 6 may not be necessary. In this instance, the test instrument B includes a base and reagent retaining portions 8A and 8B formed on the base. Each of the reagent retaining portions 8A and 8B is structured as a reagent pad provided by impregnating and drying a reagent in a carrier. The reagent retaining portions are designed for the testing of a plurality of items such that the reagent retaining portion 8A is for testing glucose while the reagent retaining portion 8B is for testing protein, for example. A test item code 63 is printed on the base to show what kind of items the test instrument B measures.

When the test instrument B is of a cuvette type, each of the compartments (hereinafter referred to as "well") in the cuvette corresponds to the carrier 7. By sealing a reagent in a liquid or solid state in the wells, the wells function as reagent retaining portions 8A and 8B. A test item code 63 may be printed on the surface of an aluminum laminate which hermetically seals the well to prevent the content from leaking out of the well. A patient information entry section 64 may also be provided on the surface of the seal.

In a test instrument B for immunochromatography, the carrier 7 is a porous member for causing the sample applied to the application portion 61 to spread over the reagent retaining portions 8A, 8B and 8C and may comprise a strip made of e.g. nitrocellulose. In a urine test strip, a biochemical test piece or a cuvette-type test instrument, the carrier 7 is a pad made of at least one of a porous film and a high molecular compound impregnated with a reagent or a well constituting the cuvette.

In this embodiment which employs immunochromatography as an example, the reagent retaining portions 8A, 8B, 8C are provided by fixing a reagent (immunologic substance such as an antibody) to part of the carrier 7. Specifically, the reagent retaining portions 8A and 8B are provided by fixing e.g. a reagent for determining positive or negative in tests for influenza. The reagent retaining portions 8A and 8B extend linearly in the width direction of the carrier 7 and are generally called a "test line". The number of reagent retaining portions 8A and 8B may be increased as desired depending on the target to be tested. Although these reagent retaining portions are generally called "test line", they may not be linear but may be in the form of a spot. In a urine test strip, the reagent retaining portion 8A is a reagent pad for testing a single item. Theoretically, therefore, when a urine test strip includes ten reagent retaining portions, the urine test strip is capable of testing ten items.

The reagent retaining portion 8C is utilized for determining whether or not the sample has properly passed through the reagent retaining portions 8A and 8B, which are the test lines, and is generally called a "control line". The reagent retaining portion 8C is provided by fixing e.g. a reagent which develops a color due to reaction with a sample and extends linearly in the width direction of the carrier 7. Unlike this, when the test instrument is an urine test strip or a cuvette-type test instrument, a reagent may not be put into the reagent retaining portion 8C so that the reagent retaining portion can be utilized as a control pad or a control well for optically canceling the influence of hemolysis or dark colored urine caused by taking a medicine, for example.

As shown in FIG. 1, the case 1 of the optical measurement apparatus A, which may be made of e.g. a resin or a metal, accommodates the reader 2, the controller 3 and the printer 4, which are the other structural elements of the optical measurement apparatus A. The case 1 includes a mount portion 11. A test instrument B to which a sample is applied is to be mounted to the mount portion 11. In this embodiment, the mount portion 11 is made up of six sections CH1-CH6 so that six test instruments B at the most can be mounted at a desired timing. A plurality of LED lamps are provided directly above the mount portion 11. When a test instrument B is mounted to the mount portion 11 at a position directly below one of the LED lamps, the LED lamp emits light of a predetermined color to indicate the mounting of the test instrument. When the test of the test instrument B is completed, the LED lamp emits light of a predetermined color to indicate the completion of the test. As shown in FIG. 2, six sensors 12 are provided at the mount portion 11. The sensors 12 are utilized for determining to which of the sections CH1-CH6 the test instrument B is mounted.

As shown in FIG. 2, the reader 2 includes light emitting modules 21A, 21B, 21C and light receiving sensor modules 22A, 22B. The light emitting modules 21A, 21B and the light receiving sensor module 22A are utilized for reading the reagent retaining portions 8A, 8B, 8C through the measurement window 62 of the test instrument B and reading the test item code 63. The light emitting module 21C and the light receiving sensor module 22B are utilized for reading the patient information entry section 64. In the reader 2, the light emitting modules 21A, 21B, 21C and the light receiving sensor modules 22A, 22B may be supported and driven collectively. Alternatively, for instance, the light emitting modules 21A, 21B and the light receiving sensor module 22A may be supported and driven separately from the light emitting module 21C and the light receiving sensor module 22B.

The light emitting modules 21A and 21B incorporate e.g. LEDs and emit light of different wavelengths. Each of the light emitting modules 21A and 21B emits linear light extending in the longitudinal direction of the test instrument B. The light receiving sensor module 22A may include a plurality of photodiodes arranged in a row or an optical sensor such as an area sensor and generates an output corresponding to the luminance of the received light. The light receiving area of the light receiving sensor module 22A is in the form of a narrow strip extending in the longitudinal direction of the test instrument B. In this embodiment, when the reader 2 is positioned directly above a test instrument B, the light receiving sensor module 22A faces the measurement window 62, and the light emitting modules 21A and 21B emit light toward the measurement window 62 at an angle of about 45 degrees from the opposite sides of the light receiving sensor module 22A. By selectively irradiating the reagent retaining portions 8A, 8B, 8C with light of different wavelengths from the light emitting modules 21A and 21B, the reagent retaining portions can be read as image data of at least two kinds of color phases.

The light emitting module 21C incorporates e.g. an LED and emits light of a predetermined wavelength. Specifically, the light emitting module 21C emits linear light extending in the longitudinal direction of the test instrument B. The light receiving sensor module 22B may include a plurality of photodiodes arranged in a row or an optical sensor such as an area sensor and generates an output corresponding to the luminance of the received light. The light receiving area of the light receiving sensor module 22B is in the form of a narrow strip extending in the longitudinal direction of the test instrument B. In this embodiment, when the reader 2 is positioned directly above a test instrument B, the light receiving sensor module 22B faces the patient information entry section 64, and the light emitting module 21C emits light toward the patient information entry section 64 at an angle of about 45 degrees.

The reader 2 is reciprocally movable directly above the six test instruments B mounted to the mount portion 11. Specifically, the reader is slidably supported by a guide bar (not shown) extending in the direction in which the six test instruments B are arranged and driven by a driving means such as a motor, a pulley or a belt (all not shown). When the reader 2 reciprocates directly above the six test instruments B, the light emitting modules 21A, 21B and the light receiving sensor module 22A read the measurement window 62 and the test item code 63 of the six test instruments B alternately. At the same time, the light emitting module 21C and the light receiving sensor module 22B successively read the patient information entry sections 64 of the six test instruments B. Even when only five or less test instruments B are mounted to the mount portion 11, the reader 2 properly performs the reading operation with respect to the mounted test instruments B. The arrangement of the test item code 63 and the patient information entry section 64 relative to the measurement window 62 may be varied. For instance, the position of the test item code 63 and that of the patient information entry section 64 may be switched. When such a test instrument B is to be used, the light receiving sensor module 22A may read the reagent retaining portions 8A, 8B, 8C and the patient information entry section 64, whereas the light receiving sensor module 22B may read the test item code 63. When the test instrument B is of the above-described cuvette type, the light emitting modules and the light receiving modules of the reader 2 are arranged on a side of the wells. Thus, while a sample is put into the wells vertically from above, the optical reading operation is performed by irradiating the wells with light in the horizontal direction and receiving the light on the opposite side through the wells.

For instance, the controller 3 includes a CPU, a ROM, a RAM and an interface. The CPU controls the entirety of the optical measurement apparatus A. The ROM stores various programs or parameters for the processing to be performed by the CPU. The RAM temporarily stores programs or measurement results. The interface performs the inputting and outputting operations of the controller 3.

The printer 4 is a device for outputting the test results of the test instrument B and incorporates e.g. a thermal printhead. As shown in FIG. 6, when the test of the test instruments B is completed in the immunochromatography apparatus A, the test results corresponding to the test item are printed.

The test using the optical measurement apparatus A will be described below using tests for influenza by immunochromatography as an example.

EXAMPLE 1

Figure 5:
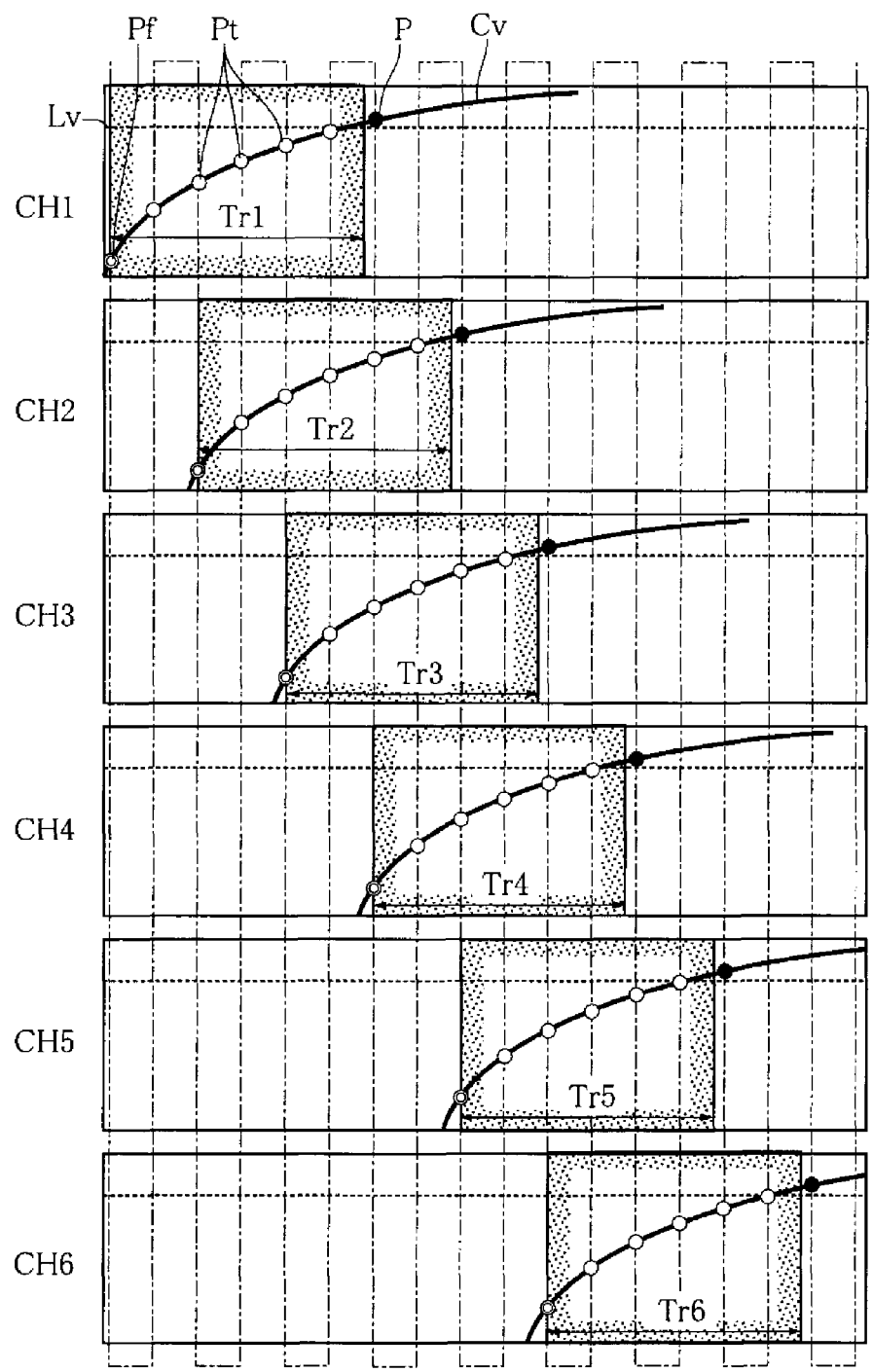
FIG. 5 is a chart showing an example of test performed with the optical measurement apparatus shown in FIG. 1.

FIG. 5 shows an example of test performed using the optical measurement apparatus A. In this figure, the horizontal axis indicates time, and each of the reaction progress curves Cv indicates the progress of reaction in a relevant one of the test instruments B mounted to the sections CH1-CH6. The reference level Lv represented by the dotted lines in the figure indicates the degree of progress of reaction above which the determination is possible to be made. The single-dashed lines in the figure indicate the route of the reciprocal movement of the reader 2 over the sections CH1-CH6. In this example, tests for influenza are performed with respect to six patients. Specifically, samples taken from six patients are applied to the respective test instruments B, and the test instruments B are successively mounted to the mount portion 11. In each of the six test instruments B, the name of the patient is written in the patient information entry section 64.

First, the test instrument B to which sample is firstly applied is mounted to the section CH1 of the mount portion 11. The sensor 12 detects the mounting of this test instrument and transmits a mount signal to the controller 3. When the reader 2 passes above the test instrument B in the section CH1 for the first time, the reader performs a reading operation Pf to read the test item code 63. In accordance with the test item represented by the test item code 63, the controller 3 sets a reaction completion period Tr1 for the section CH1. After the mounting of the test instrument to the section CH is detected by the sensor 12, the reader 2 performs a reading operation Pt for reading the reagent retaining portions 8A, 8B, 8C a plurality of times, i.e., every time it passes over the section CH1 until the reaction completion period Tr1 lapses. In this reading operations Pt, reading of the reagent retaining portions 8A, 8B, 8C is repeated. In this example, however, the results of the reading operation performed during the reaction completion period Tr1 are not used for the determination. Instead, the result of the reading operation P for reading the reagent retaining portions 8A, 8B, 8C which is performed for the first time after the lapse of the reaction completion period Tr1 is used for the determination of the influenza test. At the time point of the reading operation P, the reaction progress curve Cv is higher than the reference level Lv, because the reaction completion period Tr1 has lapsed after the mounting of the test instrument B to the section CH1.

While the test processing for the section CH1 is performed in the above-described manner, the test processing for the sections CH2-CH6 is also performed. In this example, the test item is the same for all the test instruments B in the sections CH1-CH6, so that reaction completion periods Tr1-Tr6 are the same. Thus, the reading operation is performed successively with respect to the sections CH1-CH6 in the order of mounting. As shown in FIG. 6, the test results of the samples obtained from the six patients are successively printed by the printer 4. The content to be printed includes the date and time, the identification number, the mount section (any of CH1-CH6), the test item, the test result and the name written in the patient information entry section 64. As for the patient's name, the image data of the patient information entry section 64 read by the light receiving sensor module 22B of the reader 2 is printed. To achieve clearer printing, the image data of the patient information entry section 64 may appropriately be subjected to image processing such as binarization by the controller 3.

EXAMPLE 2

Figure 7:
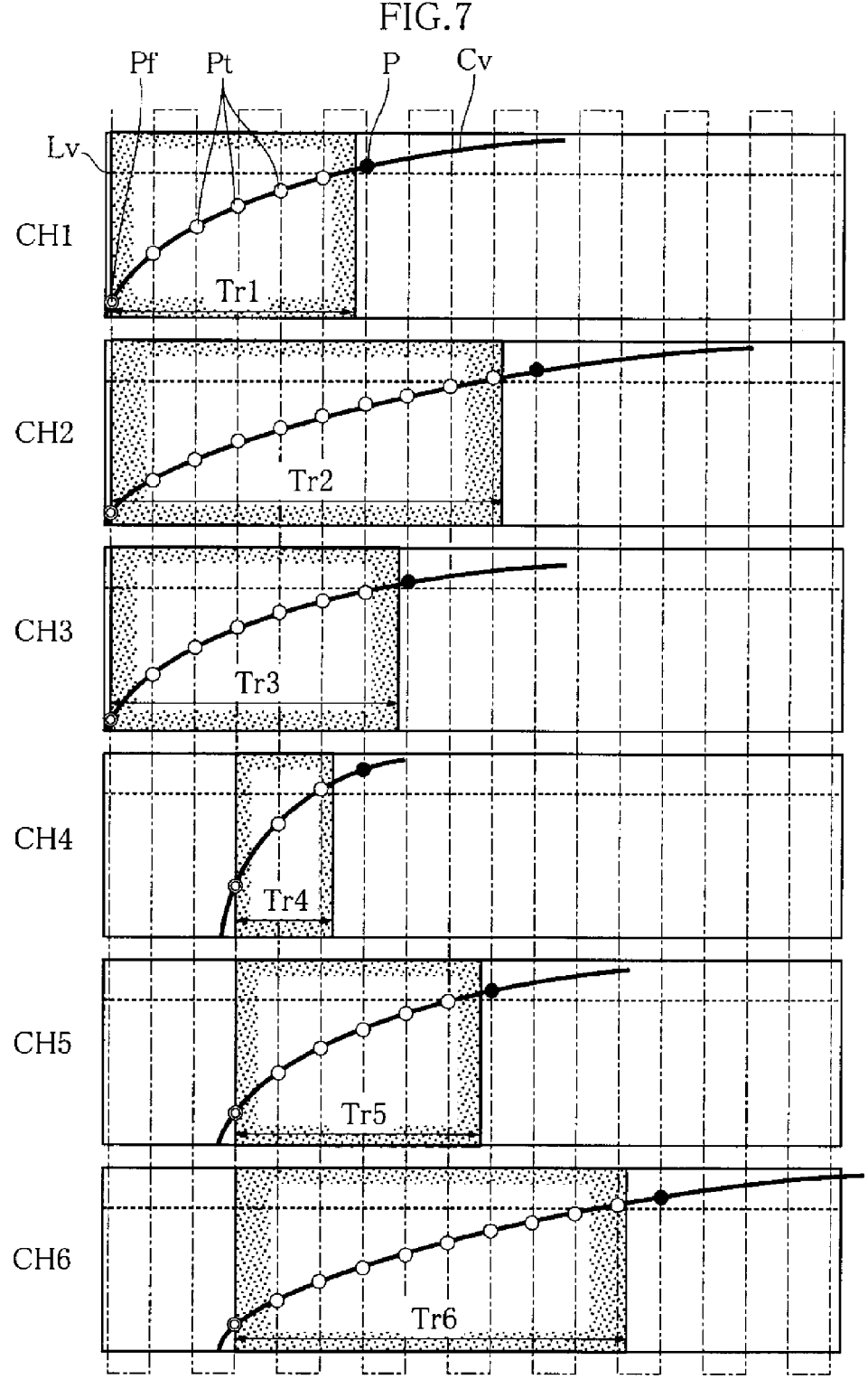
FIG. 7 is a chart showing another example of test performed with the optical measurement apparatus shown in FIG. 1.

FIG. 7 shows another example of the test performed using the optical measurement apparatus A. In this example, a sample obtained from a patient is tested for six items including allergy. First, three test instruments B are mounted to the sections CH1-CH3 of the mount portion 11. Then, another three test instruments are mounted to the sections CH4-CH6 of the mount portion 11. By performing a reading operation Pf in each of the sections CH1-CH6, the test item code 63 of each test instrument is read. Based on this, the respective reaction completion periods Tr1-Tr6 are set. Since the test items of the six test instruments B in the sections CH1-CH6 differ from each other, the reaction completion periods Tr1-Tr6 differ from each other.

In each of the sections CH1-CH6, the reading operation P is performed after the lapse of the reaction completion period Tr1-Tr6 from the time when the mounting of the test instrument B is detected by the sensor 12. In this example, the test instruments B are mounted to the sections CH1-CH3 almost at the same time. However, since the reaction completion periods Tr1-Tr3 are different from each other, the reading operation P is performed in the sections CH1-CH3 at different timings. Further, although a test instrument B is mounted to the section CH 4 later than the mounting of a test instrument B to the section CH2, the reading operation P in the section CH4 is performed earlier than that in the section CH4, because the reaction completion period Tr4 is considerably shorter than the reaction completion period Tr2. The test results of the sections CH1-CH6 are successively printed by the printer 4 in the order in which the reading operation P is completed.

EXAMPLE 3

Figure 8:
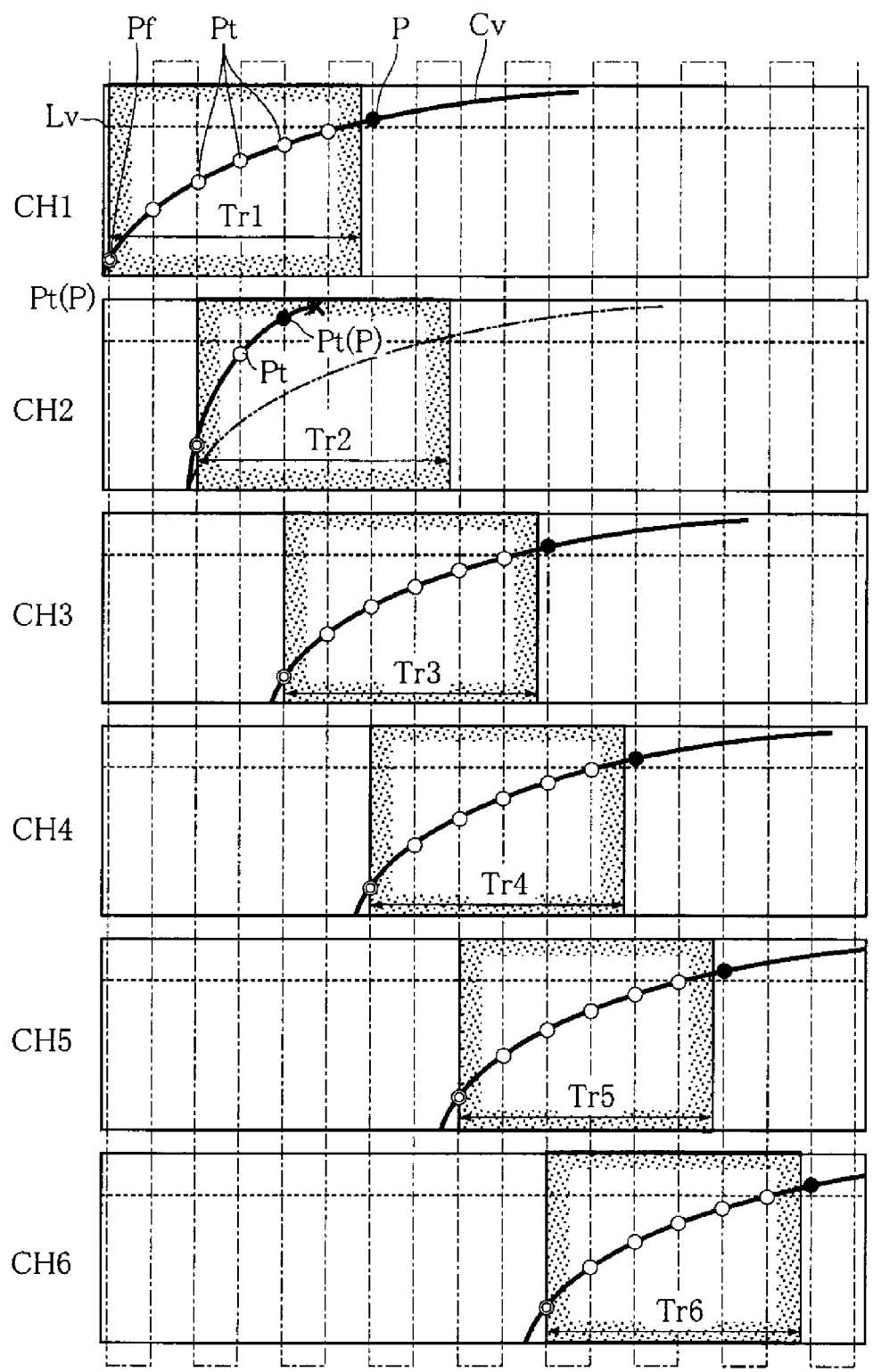
FIG. 8 is a chart showing another example of test performed with the optical measurement apparatus shown in FIG. 1.

FIG. 8 shows another example of the test performed using the optical measurement apparatus A. In this example, the program executed by the controller 3 is different from that of the above-described examples. According to this program, preliminary determination is performed using the result of a reading operation Pt performed before the reaction completion period Tr1-Tr6 lapses after the mounting of the test instrument B. Specifically, in this example, the preliminary determination is performed with respect to the section CH2 based on the result of the reading operation Pt performed after the reading operation Pf. The reaction progress curve Cv of the section CH2 is steeper than the typical reaction progress curve Cv (indicated by double-dashed lines in the figure). This indicates that the sample applied to the test instrument B in the section CH2 is reacting with the reagent at a higher speed than the normal. Thus, by the preliminary determination based on the result of the second reading operation Pt, it is found that the reference level Lv is already exceeded. Then, the controller 3 determines that the reaction in the test instrument B is completed before the lapse of the reaction completion period Tr2 and causes the printer 4 to perform printing. That is, the second reading operation Pt corresponds to the above-described reading operation P. Thus, the controller 3 finishes the test processing for that test instrument B.

The advantages of the optical measurement apparatus A will be described below.

According to the embodiment, it is possible to immediately mount a test instrument B to the optical measurement apparatus A after a sample is applied to the test instrument B. That is, after a sample is applied to the test instrument B, the user does not need to measure the time until the test becomes possible. Thus, the user can successively perform other works such as the application of a sample to another test instrument B. The test instrument B mounted to the optical measurement apparatus A is properly tested after the lapse of an appropriate time period. Thus, the optical measurement apparatus A enhances the efficiency of the test.

The reaction completion period Tr1-Tr6 is set automatically by reading the test item code 63. Thus, the user does not need to manually input the reaction completion period Tr1-Tr6 in accordance with the test item. By the operation of the sensors 12, the controller 3 grasps the accurate time at which each test instrument B is mounted. Thus, the measurement of the reaction completion period Tr1-Tr6 is automatically started.

According to the optical measurement apparatus A, the user obtains proper test results just by mounting the test instrument B to the optical measurement apparatus A. Thus, while six test instruments B at the most can be mounted in random order, the user's work does not become complicated. Thus, as described in Example 1, tests for influenza can be performed smoothly and efficiently with respect to a large number of people. Further, as described in Example 2, even when the tests for a plurality of items which require different reaction completion periods are to be performed, the work for the tests does not become complicated. The optical measurement apparatus A can automatically perform the operations from the mounting to the outputting of the test results. Thus, as the operation means for the user's operation, to provide e.g. a power button may be sufficient.

Since the reader 2 is designed to successively scan the sections CH1-CH6, the reading operations Pf, Pt, P are performed uniformly with respect to all the test instruments B mounted to the mount portion 11. The reader 2 is designed to collectively read the regions elongated in the longitudinal direction of the test instrument B, i.e., elongated perpendicularly to the scanning direction. Thus, all of the necessary reading operations are performed by the reader's scanning operation through the sections CH1-CH6. Thus, it is not necessary to perform another scanning operation in the longitudinal direction of the test instrument B in addition to the above-described scanning operation. Thus, the reading operation does not require much time.

According to the test algorism of Example 3, for the test instrument B in which the reaction of the sample with the reagent progresses faster than the expected speed, the test processing is finished before the lapse of the reaction completion period Tr2. Thus, the time taken for the test processing of the test instrument B is reasonably reduced.

EXAMPLE 4

For a test of blood by immunochromatography, the sample is generally whole blood, blood plasma or blood serum. The reaction of whole blood with a reagent tends to be weaker than that of the same amount of blood plasma or blood serum, because whole blood includes blood cell components. In this Example, test results are appropriately corrected depending on whether the sample is whole blood, or blood plasma or blood serum.

Figure 9:
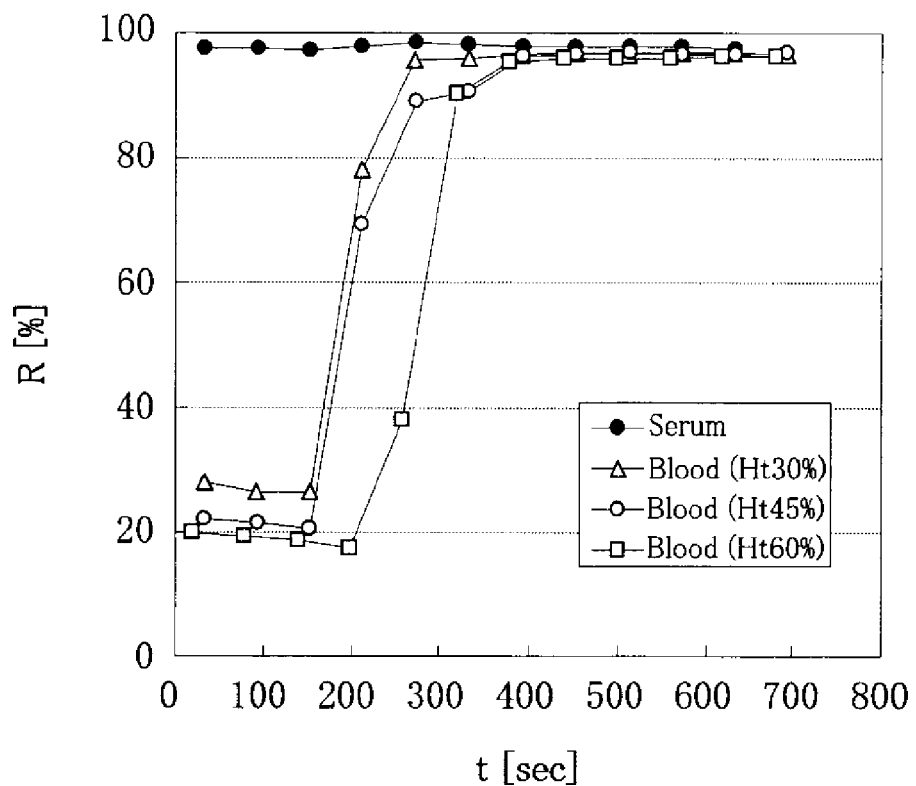
FIG. 9 is a graph showing an example of reflectance with respect to each sample.
Figure 10:
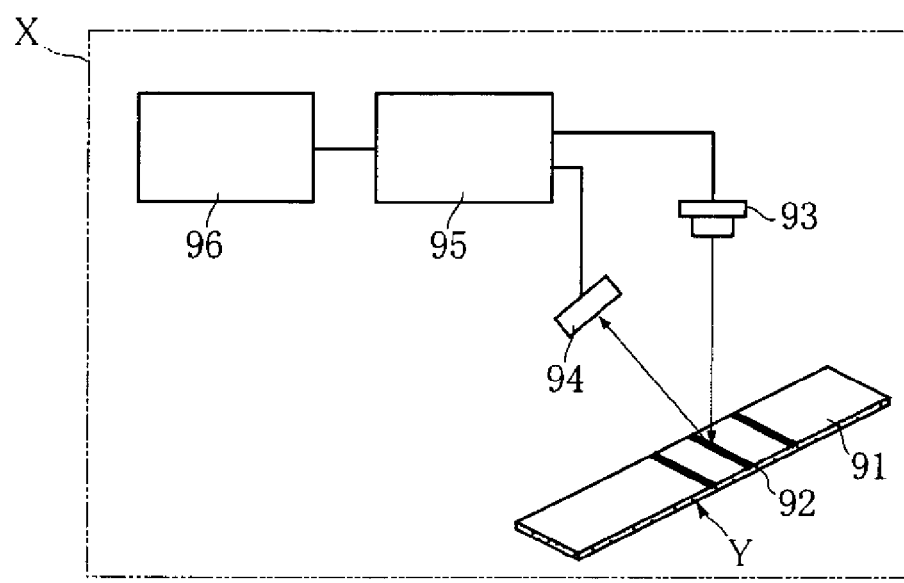
FIG. 10 is a system structure diagram of an example of conventional optical measurement apparatus.
Figure 11:
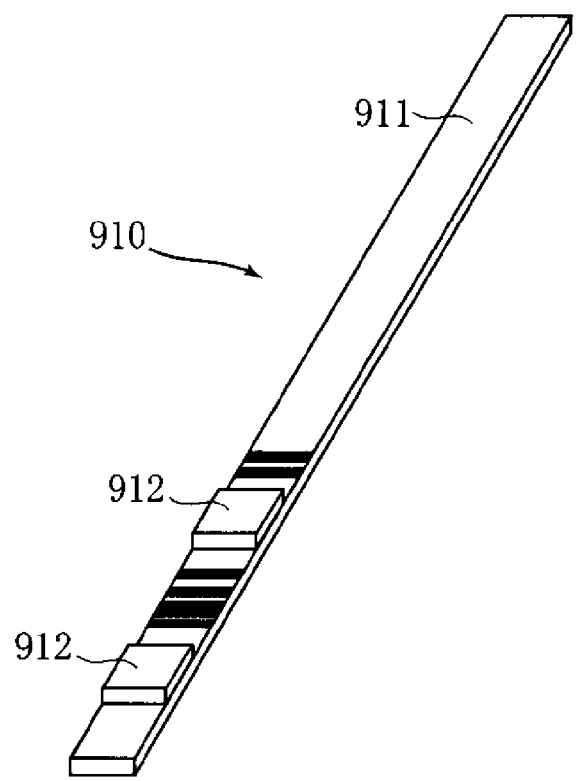
FIG. 11 is a perspective view showing an example of conventional test instrument of a test strip type.
Figure 12:
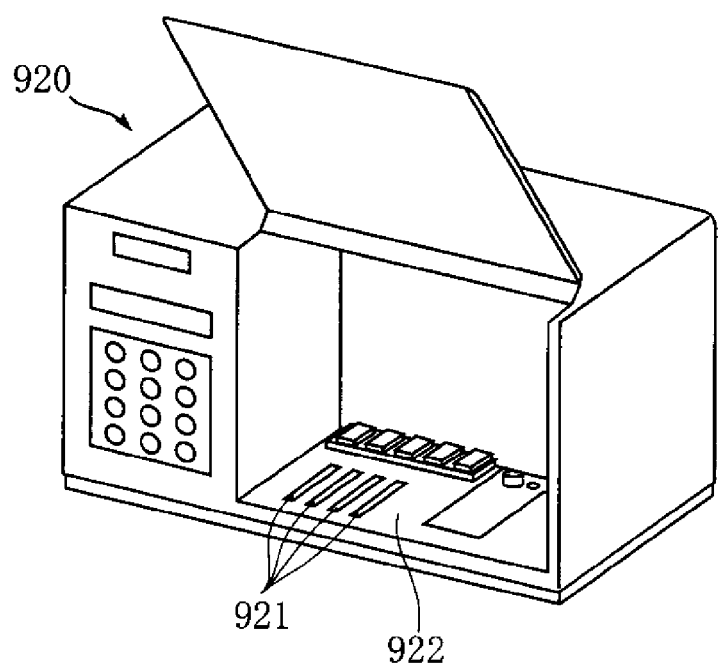
FIG. 12 is a perspective view showing an example of conventional optical measurement apparatus.
Figure 13:
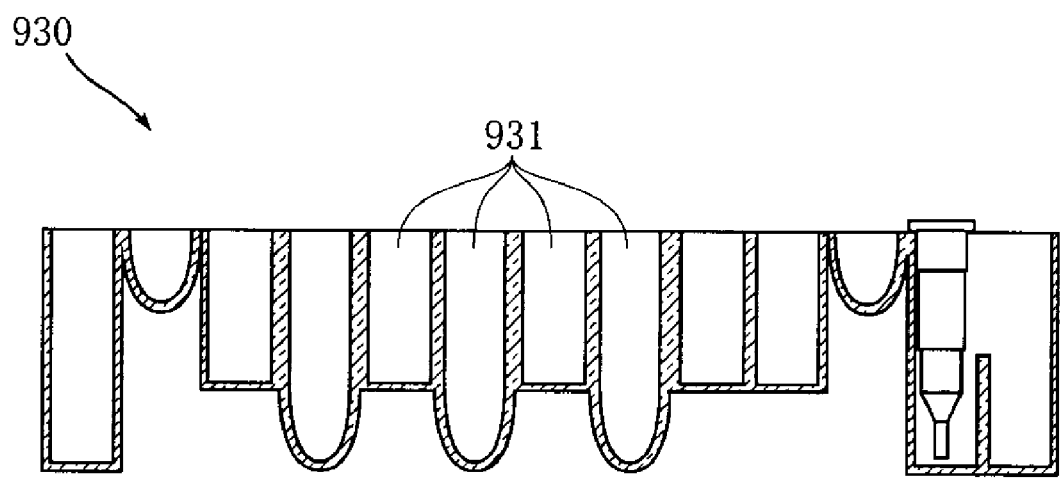
FIG. 13 is a sectional view showing an example of conventional test instrument of a cuvette type.

The reflectances of the carrier 7 when whole blood and blood serum are applied to the test instrument B are measured and shown in FIG. 9. In the figure, G1 indicates the measurements of blood serum, whereas G2-G4 show the measurements of whole blood. The Ht (hematocrit) values of G2, G3 and G4 are 30%, 45% and 60%, respectively. In the graph, the horizontal axis indicates time t, whereas the vertical axis indicates the reflectance R. The reflectance R is expressed as a percentage relative to the reflectance of a reference member such as a white plate measured in advance. As shown in the figure, when blood serum is applied, the reflectance R is close to 100% immediately after the application to the test instrument B. As will be understood from G2-G4, when whole blood as a sample is applied, the reflectance R is not more than 30% for about three minutes from the application regardless of the Ht value. After the lapse of about five minutes from the application, the reflectance R for G2-G4 become close to 100%.

In view of the above, in this Example, after the test instrument B is mounted to the optical measurement apparatus A, irradiation by the light emitting modules 21A, 21B is started, and the reflectance R is computed based on the light receiving state of the light receiving sensor module 22A. When the reflectance R becomes not more than 90% even only once within five minutes from the mounting of the test instrument, the controller 3 determines that the sample is whole blood. Then, the reference level Lv for the testing of this test instrument B is set lower than that for the testing of blood serum or blood plasma.

According to this example, the test can be performed accurately regardless of whether the sample is whole blood, blood plasma or blood serum. By determining whether the sample is whole blood, blood plasma or blood serum based on the reflectance R, correction such as resetting of the reference level Lv can be performed automatically.

Whether the sample is whole blood, blood plasma or blood serum does not necessarily need to be determined based on the reflectance R. For instance, in a structure in which blood cells in a sample are to be separated, whether the sample is whole blood, blood plasma or blood serum can be determined by checking the color change of the blood cell separation membrane before and after the blood cell separation.

The optical measurement apparatus according to the present invention is not limited to the foregoing embodiments. The specific structure of each part of the optical measurement apparatus according to the present invention may be varied in design in many ways. For instance, the number of the reagent retaining portions 8A, 8B, 8C is not limited to three, and a larger number of reagent retaining portions may be provided.

The number of the test instruments B which can be mounted to the optical measurement apparatus A is not limited to that of the foregoing embodiments but may be larger or smaller than six. As the number of the test instruments which can be mounted increases, the efficiency of the test enhances. However, even when the number of the test instruments which can be mounted is one, the apparatus still has the advantage that the user does not need to measure the reaction completion period. Although to read the test item code 63 and the patient information entry section 64 by the reader 2 is desirable for automatic testing, the present invention is not limited to this. For instance, when some burden on the user is allowed, the test item or the reaction completion period may be inputted manually by the user. As to the reader 2, it is only necessary that the reader is capable of properly reading the reagent retaining portions 8A, 8B, 8C. Thus, the emitted light and the light receiving area do not necessarily need to extend in the longitudinal direction of the test instrument B. The optical measurement apparatus of the present invention may be used for various tests in addition to tests by immunochromatography.

The invention claimed is:

1. An optical measurement apparatus to be used with a plurality of elongated test instruments mounted thereto, each of the test instruments including a carrier to which a sample is applied, the carrier being provided with a plurality of reagent retaining portions for retaining a reagent, the reagent retaining portions being spaced from each other in a longitudinal direction of each of the test instruments, the optical measurement apparatus comprising:
    a mount portion for holding the test instruments in a manner such that the test instruments are arranged side by side in a direction perpendicular to the longitudinal direction;
    a reader for reading color development at the reagent retaining portions of each test instrument; and
    a controller for performing driving control of the reader and for making a determination;
    wherein the controller performs the determination by utilizing data obtained by reading the color development of the reagent of one of the test instruments after the mounting of said one of the test instruments and lapse of a reaction completion period depending on the reagent of said one of the test instruments,
    wherein when the test instruments are arranged at the mount portion side by side in the direction perpendicular to the longitudinal direction, the reader moves relative to the mount portion in the direction perpendicular to the longitudinal direction and collectively reads the reagent retaining portions of each of the test instruments.

2. The optical measurement apparatus according to claim 1, wherein the controller causes the reader to read test item information recorded on each of the test instruments and the controller sets the reaction completion period based on the test item information.

3. The optical measurement apparatus according to claim 1, further comprising a sensor for detecting the mounting of each of the test instruments.

4. The optical measurement apparatus according to claim 1, wherein the reader performs scanning after the mounting of the test instruments and before the lapse of the reaction completion period.

5. The optical measurement apparatus according to claim 1, wherein the reader performs preliminary reading of the color development of the reagent retaining portion of each test instrument in a period between the mounting of said each test instrument and the lapse of the reaction completion period, and wherein, when reaction of the sample with the reagent is determined to be completed as a result of preliminary determination based on data obtained by the preliminary reading, the controller adopts the preliminary determination result as the determination result of said each test instrument.

6. The optical measurement apparatus according to claim 1, wherein each of the test instruments is a test piece for immunochromatography;
    wherein the carrier comprises a porous film; and
    the reagent retaining portion is provided by fixing an immunologic substance to the porous film.

7. The optical measurement apparatus according to claim 1, wherein each of the test instruments is a test strip to be dipped in a liquid;
    wherein the carrier comprises a porous film; and
    the reagent retaining portion is provided by fixing an immunologic substance in a dry state to the porous film.

8. The optical measurement apparatus according to claim 1, wherein each of the test instruments is a test piece which is so designed that a sample is to be dropped onto the reagent retaining portion;
    wherein the carrier comprises at least one of a high polymer compound and a porous film; and
    the reagent retaining portion is provided by fixing the reagent in a dry state to at least one of the high polymer compound and the porous film.

9. The optical measurement apparatus according to claim 1, wherein the test instruments are a light-transmitting cuvette including a plurality of compartments;
    wherein the carrier comprises a light-transmitting compartment; and
    the reagent retaining portion is provided by sealing the reagent in a liquid or solid state in the compartment.

10. The optical measurement apparatus according to claim 1, wherein each of the test instruments is provided with test item information, and the reader reads the test item information in addition to the color development at the reagent retaining portions.

11. The optical measurement apparatus according to claim 1, wherein the reader is provided with a plurality of light emitting modules and a plurality of light receiving sensor modules.

* * * * *